United States Patent [19]

Kopsch et al.

[11] Patent Number: 5,045,334

[45] Date of Patent: Sep. 3, 1991

[54] PROCESS FOR SEPARATING AND REMOVING CAFFEINE AND CHLOROGENIC FROM RAW COFFEE AND FROM ONE ANOTHER

[75] Inventors: Reiner Kopsch, Schenefeld; Henning Lutz, Halstenbek; Claus Gösswein, Buchholz, all of Fed. Rep. of Germany

[73] Assignee: Kaffee Handelsgesellschaft MBH, Fed. Rep. of Germany

[21] Appl. No.: 588,501

[22] Filed: Sep. 25, 1990

Related U.S. Application Data

[63] Continuation of Ser. No. 315,308, Feb. 24, 1989, abandoned.

[30] Foreign Application Priority Data

Feb. 24, 1988 [DE] Fed. Rep. of Germany ....... 3806372

[51] Int. Cl.$^5$ .................................................. A23F 5/22
[52] U.S. Cl. ..................................... 426/422; 427/271
[58] Field of Search ............................... 426/271, 422

[56] References Cited

U.S. PATENT DOCUMENTS

4,344,974 8/1982 Sirtl ..................................... 426/271

FOREIGN PATENT DOCUMENTS

WO87/04704 8/1987 World Int. Prop. O. .

OTHER PUBLICATIONS

Chemical Abstracts, 106(7):48727(b), (02-16-87).

*Primary Examiner*—Joseph Golian
*Attorney, Agent, or Firm*—Cushman, Darby & Cushman

[57] ABSTRACT

A process for separating caffeine from an aqueous raw coffee extract by means of gel chromatography is described, in which simultaneously the chlorogenic acids can be separated if desired. The inventive process makes it possible to obtain in a simple manner decaffeinated coffee, optionally with a reduced. chlorgenic acid content.

7 Claims, 8 Drawing Sheets

FIG.1
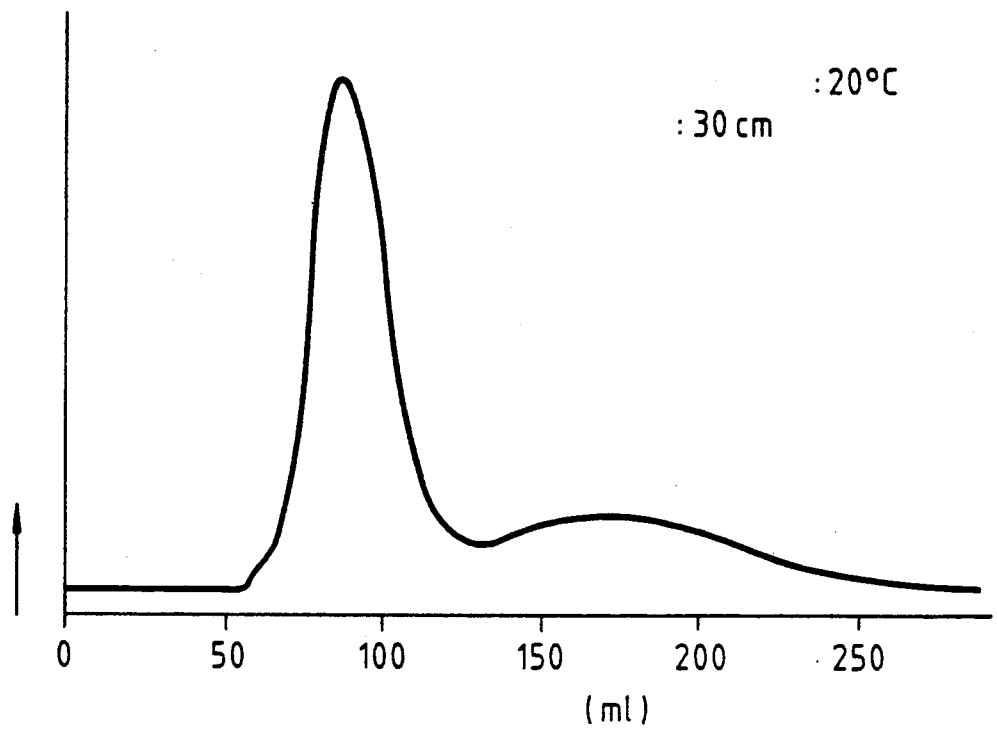
®G10
:20°C
:30 cm
(ml)
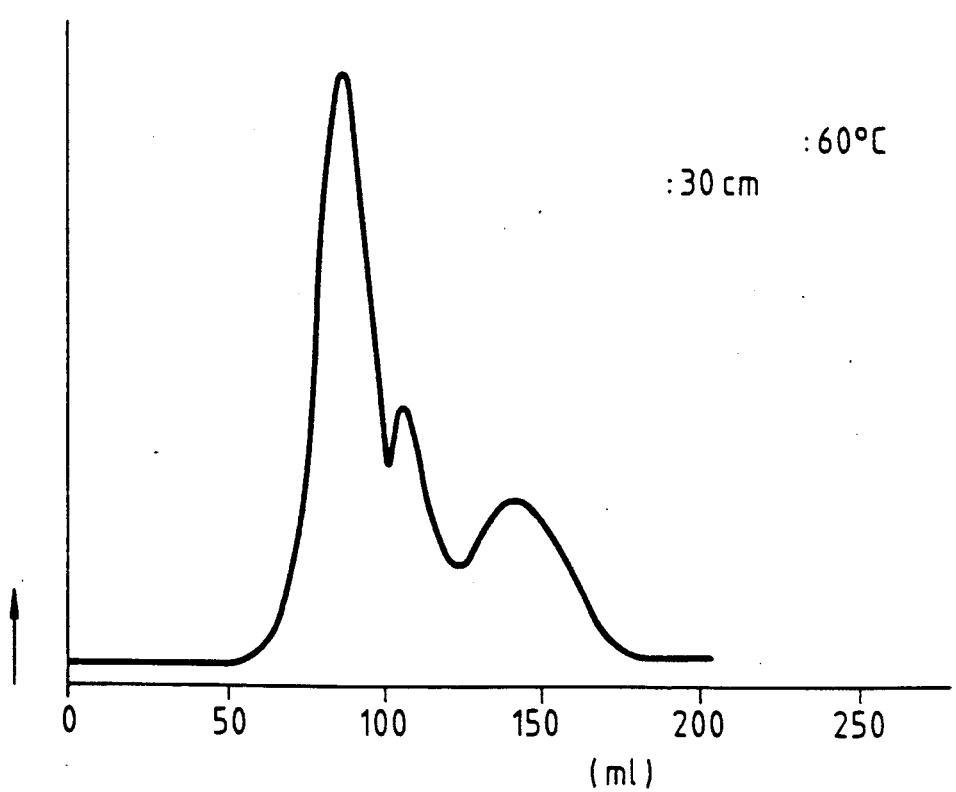
:60°C
:30 cm
(ml)

PROCESS FOR SEPARATING AND REMOVING CAFFEINE AND CHLOROGENIC FROM RAW COFFEE AND FROM ONE ANOTHER

This is a continuation of application Ser. No. 07/315,308, filed on Feb. 24, 1989, which was abandoned upon the filing hereof.

The invention relates to a process for separating and removing caffeine from raw coffee in which the raw coffee is aqueously extracted in a careful manner and the caffeine is separated from the extract by means of gel permeation chromatography. It can be subsequently recovered, simply, in a high yield and in a substantially pure form.

The separation of caffeine from aqueous raw coffee extracts is known. Thus, for example, German Patent 685 237 and European Patent application 8398 describe processes in which the caffeine is removed from aqueous extracts by adsorption on activated carbon. The disadvantage of these processes is inter alia that it is difficult to subsequently remove the caffeine from the activated carbon, and thus the carbon is not readily available for further use.

European Patent application 78088 discloses a process in which the caffeine is removed from aqueous raw coffee extracts by adsorption on suitable resins. This process requires resins having a selective and strong binding capacity for caffeine. Duolite 5761 of Diamond Shamrock is recommended as being particularly suitable.

This process is also disadvantageous in connection with the production of pure caffeine, because the latter can only be removed with difficulty with water from such resins. It is therefore recommended that the caffeine-loaded resin be treated with organic solvents, so as in this way to recover the caffeine (cf. p.8, lines 2 to 26).

The problem of the present invention is to carefully remove caffeine from an aqueous raw coffee extract in such a way that it can be recovered easily and substantially completely without the action of organic solvents, whilst simultaneously permitting the production of decaffeinated raw coffee.

Gel permeation chromatography on crosslinked dextrans is generally used for separating substance mixtures as a function of the molecular size, i.e. the molecules appear in the eluate in the order of decreasing molecule size. It is already known from EP-A-87901048.6 that crosslinked dextrans have a selective retention capacity with respect to chlorogenic acids which is independent of the molecular sieve function thereof, i.e. on selecting a dextran with a suitable degree of crosslinking, the total quantity of the admixtures or impurities contained in a raw coffee extract with a higher and lower molecular weight than the chlorogenic acid leaves the separating column in one fraction, whilst the chlorogenic acids are selectively retained. As described in EP-A-87901048.6, by further elution with water they can then be recovered in a relatively pure and cleanly separated fraction (cf. FIG. 1a).

According to the invention, it has now been surprisingly found that caffeine can be separated from a raw coffee extract by means of gel permeation chromatography on highly crosslinked, modified polysaccharides and in a selective manner from the chlorogenic acids on the one hand and the remaining impurities on the other, if the gel temperature is raised to 40 to 80, preferably 50 to 70 and in particularly preferred manner to 60° C. and the elution is performed with water at corresponding temperatures.

BRIEF DESCRIPTION OF THE DRAWINGS

FIG. 1 shows the separation patterns of the eluate according to differential refractometer measurements for the process of Example 1.

Figure 2:
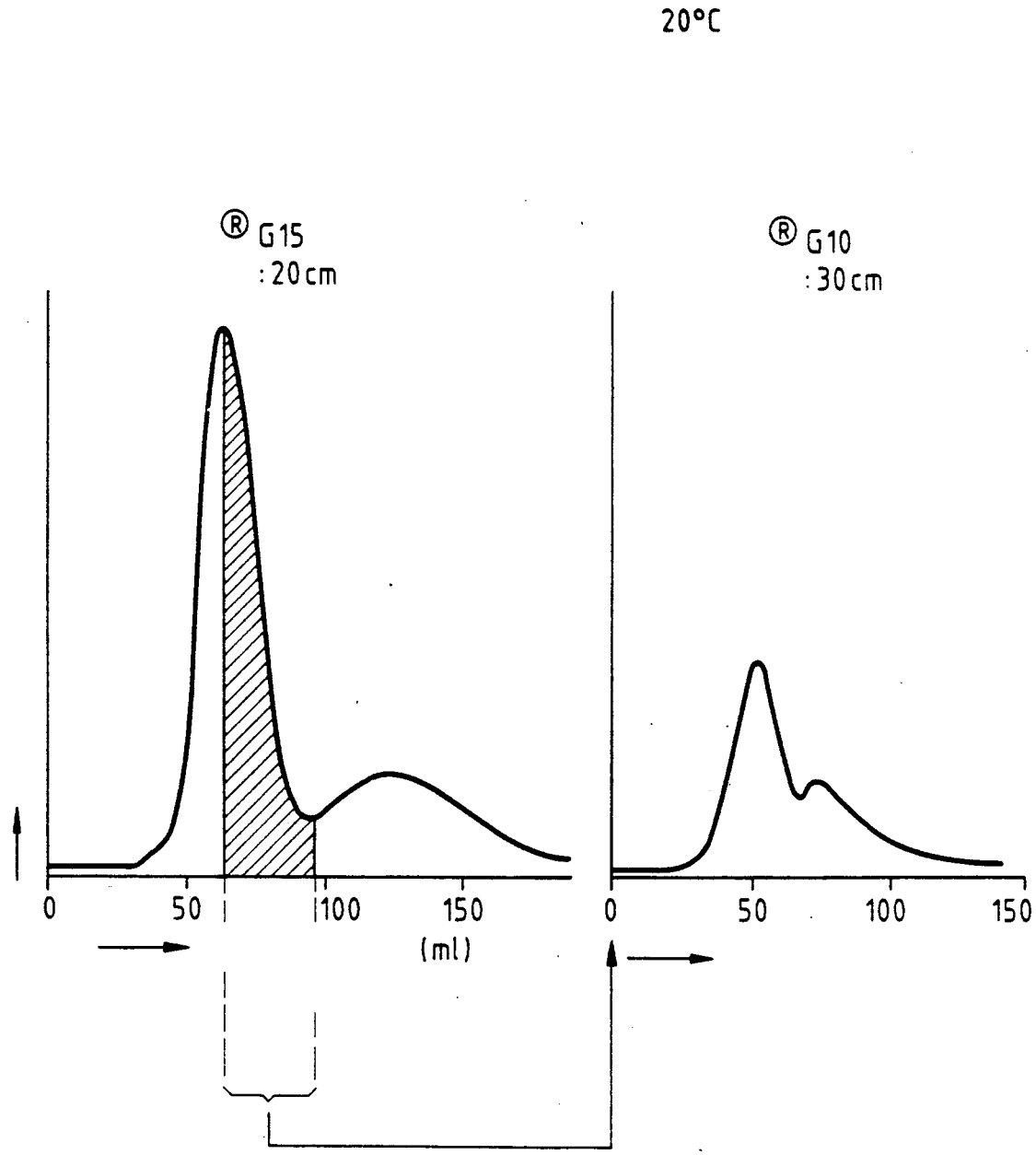
FIG. 2 shows the separation patterns of the eluate according to differential refractometer measurements for the two-column process of Example 2.

Particularly suitable materials for separation purposes are gels of crosslinked dextrans, such as those marketed under the tradename Sephadex ®. For the separation of chlorogenic acid from plant extracts, EP-A-87901048.6 already states that the separation efficiency increases with an increasing degree of crosslinking of the dextran gel used. Thus, for a given column length with more highly crosslinked dextran gel there is a more efficient separation than when using a gel with a lower degree of crosslinking, the swellability of the gel being usable as an indication of its crosslinking degree. The swellability drops with rising crosslinking degree. Thus, e.g. for producing 100 ml of swollen gel, 20 g of Sephadex ® G 25 (bed volume 4–6 ml/g) dry material are required thereby producing a bed volume of approximately 5 ml/g in a swollen state), whilst for producing the same gel volume 40 g of the much more highly crosslinked Sephadex ® G 10 (bed volume 2–3 ml/g) are required (thereby producing a bed volume of approximately 2.5 ml/g in a swollen state). Preference is given to the use of gels corresponding to the degree of crosslinking present in Sephadex ® G 15 (bed volume 2.5–3.5 ml/g) or G 10 for the separation of caffeine from a raw coffee extract.

If an aqueous raw coffee extract is e.g. applied in accordance with the inventive process to a highly crosslinked dextran gel corresponding to Sephadex ® G 10 at 60° C. and the gel is subsequently eluted with water at this temperature, then it is unexpectedly found that the extract is separated into three fractions (cf. FIG. 1b). Thus, there is in fact firstly a main fraction, which contains the total quantity of the substances contained in the raw coffee extract, with the exception of caffeine and chlorogenic acids. The caffeine appears in a clearly separated peak directly following the remaining impurities. Under the given conditions, the caffeine passage in a through-flowing, aqueous raw coffee extract is clearly and selectively delayed and it is surprisingly possible under the indicated conditions to bring about a column chromatographic separation of the caffeine from the chlorogenic acids on the one hand and the remaining impurities on the other (cf. FIG. 1b).

According to another embodiment of the invention, it is initially possible to carry out a prepurification, in that the aqueous raw coffee extract is separated in the first stage at room temperature on a dextran I with a lower degree of crosslinking, such as e.g. Sephadex G 15. As described in EP-A-87901048.6, the impurities, including the caffeine, according to the conductivity measurement are contained in a first, wide peak, which essentially appears at the column outlet with the elution front. However, according to the invention, it has surprisingly been found that even on such a gel and at room temperature the caffeine is retained to such an extent that only the eluate fraction extending from the maximum of the first peak to the appearance of the chlorogenic acid in the eluate contains caffeine (cf. FIG. 2, column I).

If the caffeine-containing fraction of this eluate in a second stage is passed onto a dextran II with a high degree of crosslinking, such as e.g. Sephadex ® G 10, it is possible to obtain at room temperature an aqueous caffeine solution which is substantially free from impurities (cf. FIG. 2, column II), whilst the chlorogenic acids can be easily eluted from gel I according to the known process.

Figure 3:
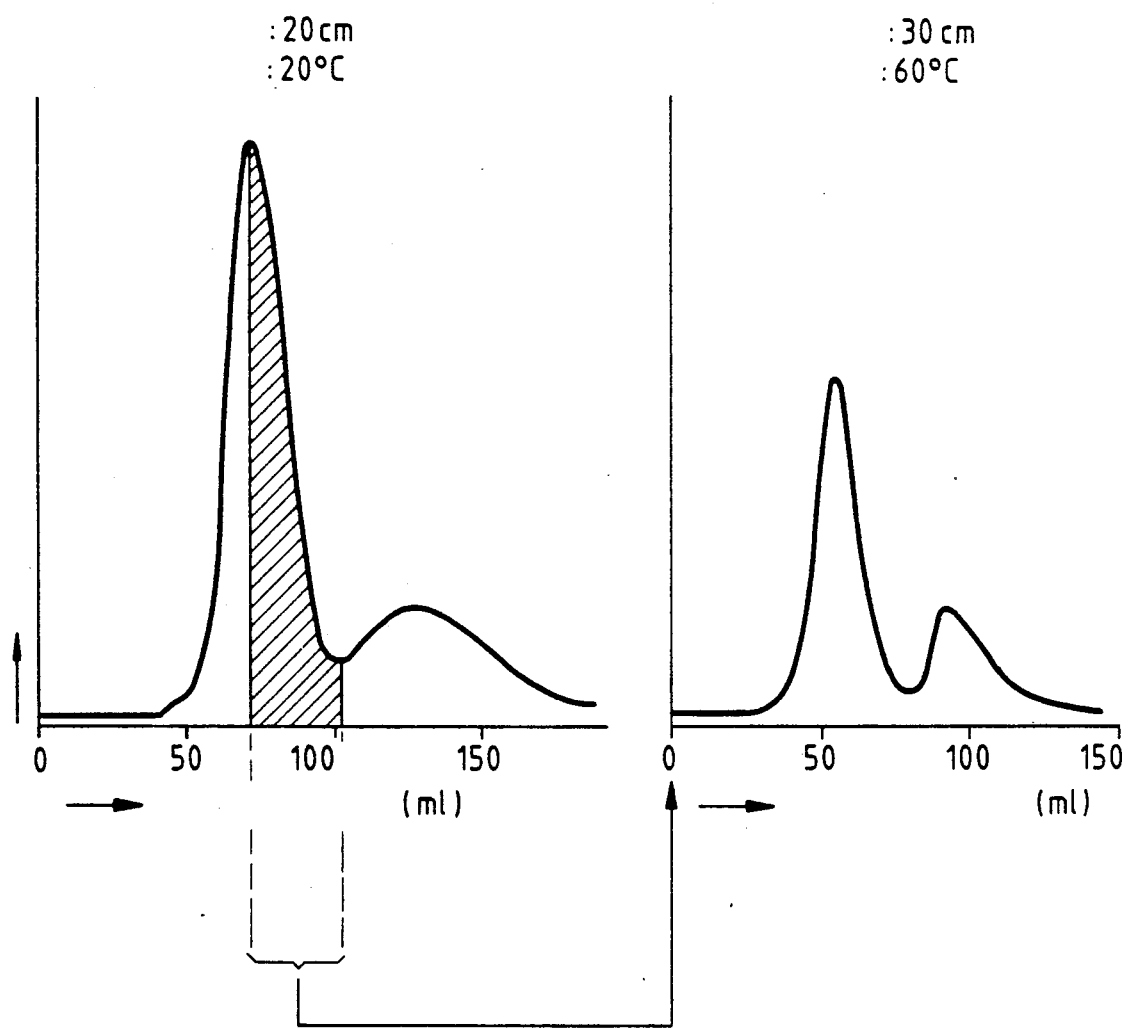
FIG. 3 shows the separation patterns of the eluate according to differential refractometer measurements for the two-column process of Example 3.

However, according to a particularly preferred embodiment of the invention, the second purification stage is performed at elevated temperature, e.g. at 40 to 80, preferably 50 to 70 and particularly at 60° C. As is revealed by the elution pattern of column II in FIG. 3, this leads to an almost complete separation of the caffeine fraction from the remaining impurities carried over from column I.

According to the invention, it has also been found that in the manner described in detail hereinafter the caffeine binds to itself a substantially constant quantity of chlorogenic acids, as a function of the temperature. The invention refers to the caffeine bound to the chlorogenic acid as the caffeine-chlorogenic acid complex (CC complex). It has been revealed that this quantity increases with rising temperature. Whilst the chlorogenic acid proportion in the total mixture of caffeine and chlorogenic acids is approximately 20 to 25% at 20° C., the chlorogenic acid fraction rises to above 40% at 60° C.

Also in view of this surprising finding, in a particularly preferred embodiment the inventive process is carried out in such a way that the prepurification is performed on a dextran I at room temperature in order to bring about a minimum chlorogenic acid content in the caffeine. The separation of the caffeine in the second stage on a dextran II with a high degree of crosslinking is then performed at 60° C., so as in this way to achieve a very clean separation from the impurities carried over into the second stage (cf. FIG. 3).

It has also been revealed by this invention that the CC complex can be split by concentrating of the solution (cf. Example 9) to obtain pure caffeine.

The aqueous raw coffee extract used in the inventive process can be prepared in that the raw coffee is brought to a water content of approximately 50% and is extracted in a continuous process at temperatures of 60° to 100° C. for 2 to 4 hours and preferably 3 hours. This extract is introduced into the inventive separating process.

For the production of decaffeinated raw coffee, the eluate fractions containing all the impurities and chlorogenic acids, as well as the chlorogenic acids split off from the CC complex combined into a process solution by dehydration can again be brought to the extract starting concentration and again pass through a raw coffee, e.g. in the manner described in DE-OS 31 19 277. For this purpose the process solution can be allowed to act in constant motion on premoistened raw coffee at temperatures of 60° to 100° C. for 2 to 4 and preferably 3 hours. Since, with the exception of the caffeine content, the process solution is in equilibrium with the raw coffee constituents, it will only remove the caffeine from the same. Thus, through continuous performance of the process, it is possible to produce in a careful manner decaffeinated coffee and simultaneously recover the removed caffeine from the aqueous solution.

An aqueous extract with a high caffeine content can be obtained in that the caffeine-free process solution, which has been adjusted to the starting concentration with respect to the remaining constituents, is passed in a counterflow process through a series of raw coffee fractions with increasing caffeine content, the freshly purified process solution always encountering the fraction with the lowest caffeine content. If this process is performed continuously each coffee fraction is extracted several times and the caffeine can in this way be completely removed. At the same time the separating column is continuously supplied with a process solution with a high caffeine content.

According to a particularly preferred embodiment of the invention caffeine and chlorogenic acids are simultaneously separated from an aqueous raw coffee extract and optionally recovered. For this purpose only the fractions of the eluates not containing caffeine and chlorogenic acids (NCC fractions) are combined to form a process solution, whereas the fractions containing the caffeine and chlorogenic acids are separately collected. In the sense of the present invention, the term "chlorogenic acids" covers monocaffeoyl-quinic acids.

The process of the invention can be performed in that an aqueous extract containing caffeine and chlorogenic acids and obtained from raw coffee in the manner described hereinbefore is initially separated at room temperature on a first column I containing a gel with a lower degree of crosslinking, such as e.g. Sephadex ® G 15. As stated hereinbefore, in this procedure the impurities, including the caffeine, leave the column in a broad fraction, whereas the chlorogenic acids are initially retained and only appear as a separate fraction after prolonged elution with water.

As stated hereinbefore, a differentiation occurs in the broad fraction containing the impurities and the caffeine to the extent that the caffeine within this fraction only leaves column I after reaching the first maximum in accordance with the recording of the separating pattern based on the conductivity and the signal of the differential refractometer.

Therefore the process is preferably performed in such a way that the first fraction of the eluate from the initial rise to the first maximum of the recorded separating pattern is separately collected as NCC fraction I. The elution process is discontinued on reaching the maximum and the outlet of the column containing a gel such as Sephadex ® G 15 is connected to the inlet of a second column II, which is longer than the first column and contains a more highly crosslinked gel. For example, the length of the column can be 30 cm and it can contain approximately 150 ml of Sephadex ® G 10. The caffeine-containing eluate leaving the first column is now passed to the second column until chlorogenic acid appears at the outlet of the first column. At this point the elution process is again interrupted and the columns separated from one another. The columns are now separately eluted with deionized water, followed by elution from the first column of the chlorogenic acids and from the second column of the remaining impurities as NCC fraction II, as well as the purified caffeine.

As explained hereinbefore, also in this inventive embodiment, the second column II can be kept and eluted at room temperature, but preferably the temperature of column II is raised to 40 to 80, preferably 50 to 70 and in a particularly preferred manner to approximately 60° C. and the column is eluted at these temperatures so that, as stated hereinbefore, a better separation efficiency is obtained.

On performing the above process in a continuous manner the NCC fractions I and II as well as the fraction containing the chlorogenic acid are combined to form a process solution, which is set to the initial concentration and brought into contact with fresh or partly extracted raw coffee. For this purpose, the raw coffee is preferably set to a water content of approximately 50%. It is subsequently contacted with the concentrated process solution, whose composition corresponds to the fresh extract passing out, but contains no caffeine. In accordance with known methods, the process solution is now brought into equilibrium with the raw coffee. Now only the caffeine missing in the process solution is removed from the coffee, i.e. the "gap" in the spectrum of the components is filled.

Particularly advantageous results can be obtained by continuously passing the caffeine free (NCaf) process solution through a series of raw coffee fractions in a counterflow process. This leads to a concentration gradient within the raw office fractions, the freshly purified solution always encountering the fraction with the lowest content of caffeine. It is therefore possible to continuously produce raw coffee with a very low caffeine content and simultaneously feed a high content process solution into the separating device.

The speed of the selective extraction or the time up to the setting of the equilibrium can be adjusted by the temperature and stirring speeds. As caffeine and chlorogenic acid are extracted at different speeds from the raw coffee beans, it is possible to influence the ratio of the chlorogenic acid and the caffeine in the treated coffee by corresponding process control. It is also possible to extract the two components in a different ratio from the coffee by varying the concentration of the corresponding components in the process solution.

Figure 5:
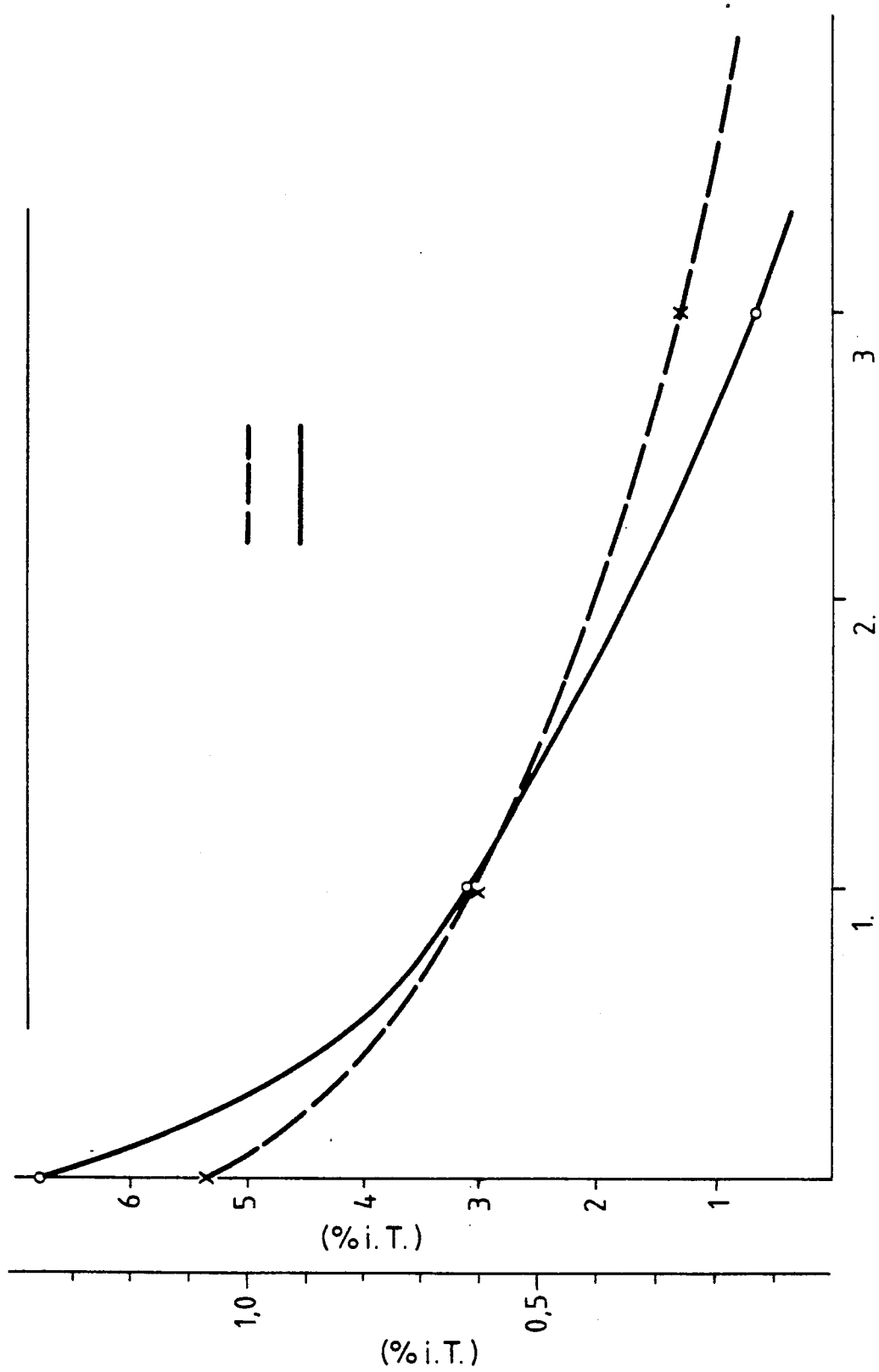
FIG. 5 depicts the HPLC peak patterns of the starting solution and the individual fractions after separation for the process of Example 6.

It has been found that, in accordance with the inventive process, the NCC fractions could be almost completely freed from chlorogenic acids and caffeine. The chlorogenic acid was also obtained almost free from caffeine. As explained hereinbefore, it has not hitherto been possible to completely free the caffeine fraction from chlorogenic acids (cf. FIG. 5).

Figure 6:
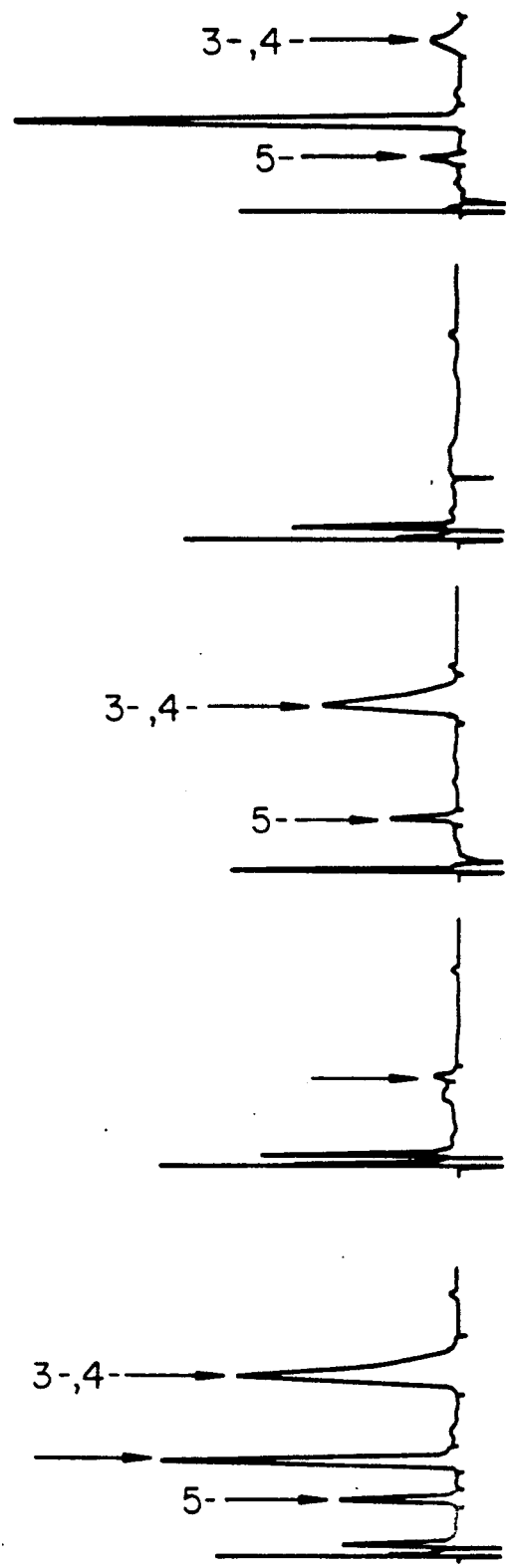
FIG. 6 depicts the HPLC patterns for the three separations performed in Example 8.

It was possible to prove in separation tests using model mixtures with constant caffeine and varying chlorogenic acid quantities, that the caffeine firmly binds to itself a clearly defined chlorogenic acid quantity (cf. FIG. 6). As stated hereinbefore, this quantity is also dependent on the solution temperature.

However, it has surprisingly been found according to the invention that the bond between the chlorogenic acid and the caffeine observed in dilute solutions is broken on concentration. Thus, if an aqueous eluate containing approximately 0.3% caffeine (cf. Example 2) is concentrated approximately 100 times, the caffeine is precipitated as a solid substance with a purity level of almost 100% according to HPLC analysis (cf. Example 9). The precipitation rate of pure caffeine can be increased by cooling as a result of the described temperature effect.

Thus, the invention provides the possibility for producing pure caffeine without using organic solvents.

The invention is illustrated hereinafter by means of examples.

EXAMPLE 1

300 g of Columbia raw coffee with a moisture content of 8.30% were mixed with 1500 ml of water and kept at 80° C. for 3 hours and accompanied by simultaneous vibration in a water bath. The extract was then separated from the coffee beans. It had a pH-value of 5.56 and was concentrated to 160 ml.

The extract had a dry substance content of 24.19%, a chlorogenic acid content of 4.82% and a caffeine content of 1.55%, in each case based on the liquid concentrate.

Small particles contained were separated from the solution by centrifuging at 3000 g. 15.0 g of this extract were supplied to a 20 cm long and diameter 2.5 cm column containing 150 ml of Sephadex ® G 10. The column temperature was approximately 20° C. The column was subsequently eluted at a flow rate of 200 ml/h with deionized water at a temperature of approximately 20° C. The eluate passing out was passed through the measuring cell of a differential refractometer and continuously collected.

The fractions underwent HPLC analysis under the following conditions:
Column: Waters 8 C 18 10μ Radialpak.
Mobile phase: 1.5% tetrahydrofuran + 0.1% acetic acid in water.
Flow rate: 4 ml/min.
Detector: Waters, model 440 at 280 nm.
Integrator: Shimadzu CR 3 A.

The elution pattern according to the differential refractometer measurement is given in FIG. 1a. It reveals the raw extract separation into two fractions known from EP-A-87901048.6 under the given conditions, the second fraction containing the chlorogenic acids in a substantially pure form.

The above-described process was repeated with the difference that the column was heated to a temperature of approximately 60° C. and the elution was performed with water of about this temperature.

The separation pattern of this column is given in FIG. 1b. As shown by the latter, three clearly separated fractions were obtained, which were separately collected and analysed as given in FIG. 1b.

The dry substance content was determined by evaporating partial quantities for 16 hours in the drying oven at 105° C. The chlorogenic acid and caffeine analyses were performed in the manner described hereinbefore with HPLC.

The analytical results of the individual fractions are given in Table 1.

TABLE 1

| Fraction No. | Quantity (g) | Dry substance (g/100 g) | Chlorogenic acid g/100 g | Chlorogenic acid % based on dry substance | Caffeine g/100 g | Caffeine % based on dry substance |
| --- | --- | --- | --- | --- | --- | --- |
| 1 | 60 | — | — | — | — | — |
| 2 | 53 | 4.040 | 0.011 | 0.3 | 0.009 | 0.2 |
| 3 | 25 | 2.178 | 0.613 | 28.3 | 0.873 | 40.1 |
| 4 | 66 | 1.138 | 0.831 | 73.0 | 0.019 | 1.7 |

As is apparent from Table 1, initially a precursor of approximately 60 g is obtained, which is free from extract constituents. This is followed by fraction 2, which contains most of the extract constituents, but virtually no chlorogenic acid and no caffeine. Fraction 3 contains almost all the caffeine contained in the raw coffee extract and part of the chlorogenic acids. However, fraction 4 contains the chlorogenic acids in an almost pure form.

EXAMPLE 2

Separation of a raw coffee extract using a 2-column method into NCC, caffeine and chlorogenic acid fractions at 20° C.

15 g of the concentrate according to Example 1 were fed on a column I of length 20 cm and diameter 2.5 cm and containing 100 ml of Sephadex ®G 15. The column was then eluted with deionized water at room temperature and at a flow rate of 200 ml/h. The eluate was monitored by means of a differential refractometer test signal and continuously collected. On reaching the first peak maximum elution was interrupted and the eluate passing out was passed to a second column II having a length of 30 cm, a diameter of 2.5 cm and containing 150 ml of Sephadex ®G 10. The temperature of column II was also 20° C. On reaching the first minimum, the columns were again separated from one another and the eluate of the first column continuously collected in the manner described hereinbefore. The second column was then eluted under the same conditions as given hereinbefore. The separation pattern of the two columns I and II is given in FIG. 2.

The eluates of columns I and II were in each case combined to the following fractions:
1. First runs:
Eluates without extract constituents from columns I and II.
2. NCC fraction:
Eluate from column I from the initial curve rise to the maximum of the first peak and eluate from column II from the curve rise to the inflection point of the first peak.
3. Chlorogenic acid fraction:
Eluate from column I as from the inflection point of the first peak to the end of the second peak.
4. Caffeine fraction:
Eluate from column II as from the inflection point of the first peak to the end of the second peak.

TABLE 2

| | Total Extract | | Chlorogenic acids | | Caffeine | |
| --- | --- | --- | --- | --- | --- | --- |
| | Quantity g | Dry substance content g/100 g | Concentration g/100 g | Extract % fraction | Concentration g/100 g | Extract % fraction |
| Raw Coffee Extract Column I | 15.0 | 24.19 | 4.82 | 19.93 | 1.55 | 6.41 |
| first run | 43 | — | — | — | — | — |
| NCC fraction I | 34 | 3.77 | 0 | 0 | 0.02 | 0.53 |
| Chlorogenic acid fraction Column II | 110 | 0.76 | 0.55 | 73.37 | 0 | 0 |
| first run | 58 | — | — | — | — | — |
| NCC fraction II | 49 | 1.77 | 0 | 0 | 0.003 | 0.17 |
| Caffeine fraction | 77 | 0.55 | 0.09 | 16.36 | 0.31 | 56.36 |

As is shown by Table 2, initially a first run quantity of 43 g, which is free from extract constituents is obtained from Column I. With the elution front then appears the NCC fraction I, which contains no chlorogenic acids and substantially no caffeine. After reversing the eluate, the fraction containing the chlorogenic acids is obtained and is free from caffeine.

From column II, following onto the first run with the elution front NCC fraction II is obtained and is free from chlorgenic acids and substantially free from caffeine. Then, in a clearly separated peak, the caffeine fraction of the eluate is obtained, which however still contains chlorogenic acids.

EXAMPLE 3

The process of Example 2 was repeated with the difference that column II was heated to a temperature of approximately 60° C. and eluted with deionized water at this temperature. The separation patterns of columns I and II according to this embodiment are given in FIG. 3. It can be seen that at 60° C. there is a markedly better separation of the caffeine from the remaining impurities in column II than is the case at 20° C. (cf. FIG. 2).

EXAMPLE 4

Selective extraction of caffeine and chlorogenic acid from Colombia raw coffee with the NCC process solution 54.5 g of Colombia raw coffee with an initial moisture content of 8.30% were mixed with 45.5 g of water in a 250 ml polyethylene bottle to obtain a moisture content of approximately 50% and were agitated for 30 minutes by means of a vibrator in a water bath at 80° C. 125 g of a process solution were then added, having been obtained by combining NCC fractions I and II according to Example 2. The mixture was moved for 300 minutes under the aforementioned conditions and at regular intervals 1 ml samples were taken, to determine the caffeine and chlorogenic acid content of the liquid.

Figure 4:
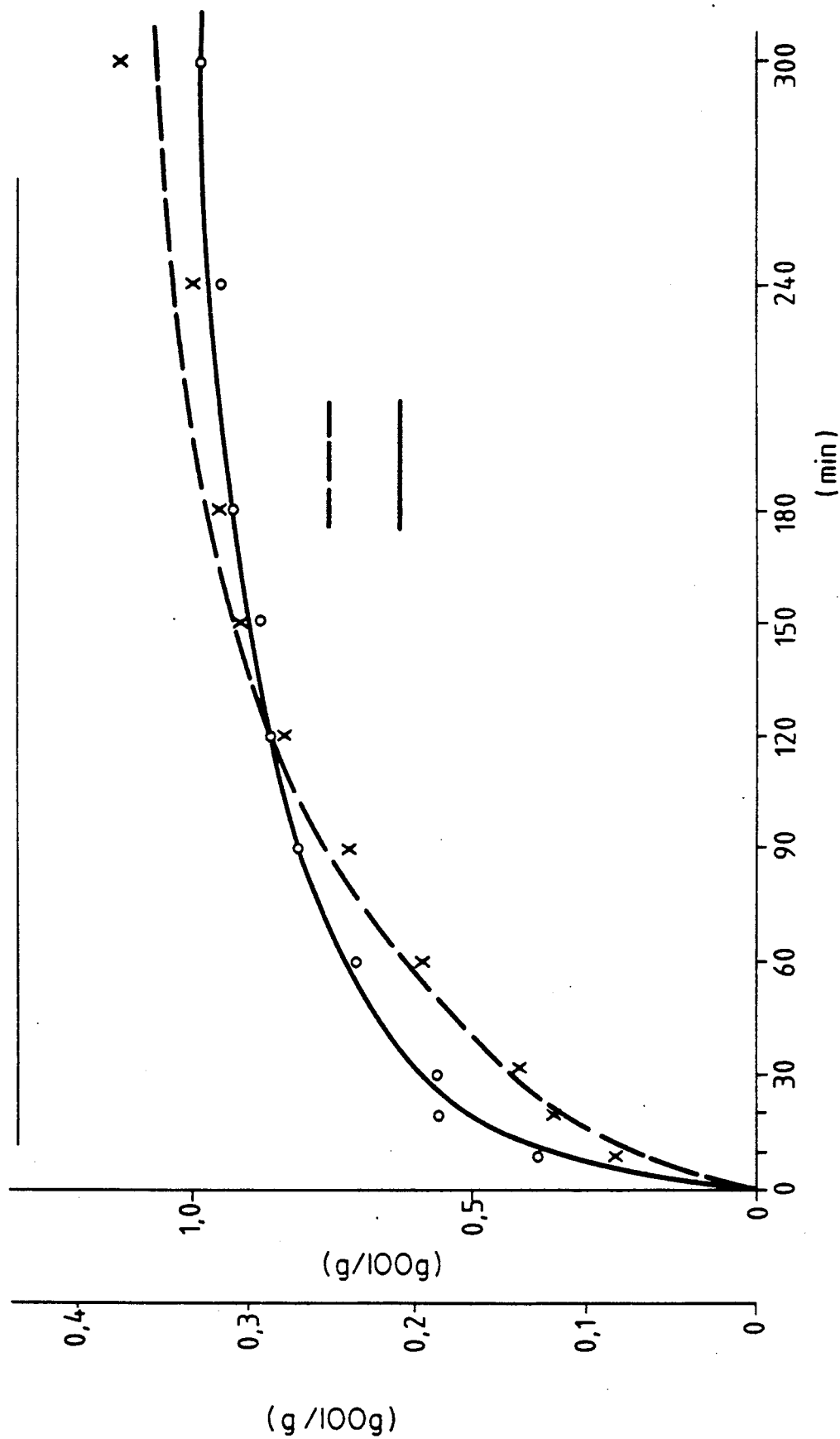
FIG. 4 shows the extraction pattern for caffeine and chlorogenic acid in the selective extraction process of Example 4.

The caffeine and chlorogenic acid contents of the process solution after 30 and 300 minutes incubation time are compared with the initial coffee in Table 3. The extraction pattern is shown in FIG. 4.

TABLE 3

|  | Chlorogenic acid concentration g/100 g | Caffeine conc. g/100 g | Chlorogenic acid/caffeine quotient |
|---|---|---|---|
| Process solution after 30 min. | 0.42 | 0.19 | 2.21 |
| Process solution after 300 min. | 1.13 | 0.33 | 3.42 |
| Initial coffee | 5.35 | 1.36 | 3.93 |

The results show that caffeine and chlorogenic acids can be simultaneously extracted with NCC process solution from raw coffee. However, the substances are extracted at different speeds and in particular at the start of the extraction time caffeine passes more rapidly into the process solution than chlorogenic acids. However, after an extraction time of 300 minutes, equilibrium was achieved and the quotient of the chlorogenic acid and caffeine roughly corresponded to that in the initial coffee (cf. Table 3).

EXAMPLE 5

Multistage selective extraction of caffeine from Columbia raw coffee

The process according to Example 4 was repeated with the difference that the same raw coffee charge was brought into equilibrium several times with fresh caffeine-free (NCaf) process solution, in order to further lower the caffeine content.

The raw coffee was pretreated in the manner described in Example 3 and successively brought into equilibrium three times for 3 hours at 80° C. with a NCaf process solution having a total dry substance content of approximately 15% and which was substantially free from chlorogenic acids and caffeine (cf. Table 5). (It was revealed during preliminary tests that a thus adjusted NCaf process solution removed no NCaf constituents from raw coffee adjusted to a 50% moisture content).

As described in Example 4, the extraction stages were performed in closed polyethylene bottles and in a thermostatically controllable vibrator. At the end of each extraction stage coffee and process solution was separated from one another on a sieve and the process solution HPLC analysed (cf Table 5). After extracting three times the raw coffee was reweighed and dried in the drying oven at 103° C. for 16 hours for moisture determination. It was then ground and its caffeine contents HPLC analysed. The HPLC analyses were carried out in the manner described in Example 1.

The results are given in Tables 4 and 5.

TABLE 4

|  | Total moist coffee weight g | Water content % | Total dry coffee weight g | Caffeine content % |
|---|---|---|---|---|
| Initial coffee | 54.5 | 8.30 | 50.0 | 1.36 |
| Treated coffee | 103.2 | 54.25 | 47.2 | 0.13 |

TABLE 5

|  | Quantity g | Total Extract | | Caffeine | |
|---|---|---|---|---|---|
|  |  | Conc. g/100 g | Quantity g | Conc. g/100 g | Quantity g |
| NCaf Starting solution | 125.0 | 14.73 | 18.41 | 0 | 0 |
| Process solution 1 | 115.3 | 16.66 | 19.21 | 0.30 | 0.35 |
| Process solution 2 | 122.2 | 15.92 | 19.45 | 0.15 | 0.18 |
| Process solution 3 | 124.4 | 15.19 | 18.85 | 0.06 | 0.07 |

The results show that the caffeine content of the treated raw coffee can be lowered from 1.36 to 0.13% based on the dry weight of the coffee.

EXAMPLE 6

Preparation of a process solution enriched with caffeine and chlorogenic acids

A NCC process solution with a dry substance concentration of 15% and largely free from caffeine and chlorogenic acids (cf. Table 6), in accordance with the process of Example 4, was successively brought three times into equilibrium for 3 hours at 80° C. with in each case 50 g of fresh Colombia raw coffee (moisture content approximately 50%). Between the individual stages, the coffee and the process solution were separated from one another on a sieve and the process solution HPLC analysed. The results are given in Table 6.

TABLE 6

|  | Quantity solution g | Total Extract | | Chlorogenic acid | | Caffeine | |
|---|---|---|---|---|---|---|---|
|  |  | Conc. g/100 g | Quantity g | Conc. g/100 g | Quantity g | Conc. g/100 g | Quantity g |
| NCC Starting solution | 125.0 | 14.73 | 18.41 | 0.04 | 0.05 | 0 | 0 |
| Process solution | 98.6 | 19.47 | 19.20 | 2.20 | 2.17 | 0.66 | 0.65 |

The results show that according to the described process the caffeine content of the process solution could be raised to 0.66 g/100 g and the chlorogenic acid content to 2.20 g/100 g.

EXAMPLE 7

The process solution containing caffeine and chlorogenic acids obtained according to the process of Example 6 was separated into NCC fractions, chlorogenic acids and caffeine on two dextran gels I and II according to the process of Example 2.

The results are given in Table 7. The HPLC peak patterns of the process solution prior to separation, the NCC fractions I and II and the chlorogenic acid and caffeine fractions are given in FIG. 5.

TABLE 7

|  | Total Extract | | Chlorogenic acids | | Caffeine | |
|---|---|---|---|---|---|---|
|  | Quantity g | Dry substance content g/100 g | Conc. g/100 g | Extract % fraction | Conc. g/100 g | Extract % fraction |
| Process solution Column I | 15.0 | 19.47 | 2.20 | 11.30 | 0.66 | 3.39 |
| first run I | 41 | — | — | — | — | — |
| NCC fraction I | 36 | 3.59 | 0 | 0 | 0.004 | 0.11 |
| Chlorogenic acid fraction Column II | 100 | 0.41 | 0.28 | 68.29 | 0 | 0 |
| first run II | 57 | — | — | — | — | — |
| NCC fraction II | 63 | 1.53 | 0 | 0 | 0 | 0 |
| Caffeine fraction | 66 | 0.21 | 0.04 | 19.05 | 0.14 | 66.67 |

The results show that the NCC fractions I and II obtained from columns I (Sephadex®G 15) and II (Sephadex®G 10) could be freed from caffeine and chlorogenic acids, with the exception of small residual quantities. Therefore these fractions are suitable for use as process solutions in continuous processes for the selective extract ion of caffeine and optionally chlorogenic acids from raw coffee.

The separation on columns I and II corresponded to the pattern given in FIG. 2.

The individual fractions obtained from columns I and II are HPLC analysed as described in Example 1. The results are given in FIG. 5, the absolute peak heights lacking significance for the present case, because the samples used for analysis had different dilution rates.

On the basis of the process of the present example caffeine was obtained with a purity of 66.67% and chlorogenic acids with a purity of 68.29%.

EXAMPLE 8

Separation of model mixtures of chlorogenic acid and caffeine

To investigate the mechanism of binding chlorogenic acids to caffeine, three model solutions were prepared, in which the caffeine content was constant, but the chlorogenic acid contents differed (cf. Table 8).

The pH-value of the solutions was in each case 5.8. All the separations were performed at 20° C. on 30 cm long, diameter 2.5 cm columns filled with in each case 150 ml of Sephadex®G 10. The separation patterns were followed by means of conductivity measurements and the differential refractometer signal. As only chlorogenic acids could be detected with the conductivity measurement, comparison of the two test signals simultaneously made it possible to measure the chlorogenic acid proportion in the particular fraction. The chlorogenic acids and the caffeine in the fractions were measured by HPLC as described in Example 1. The results are given in FIG. 6 and Table 8.

TABLE 8

|  | Initial Solution | | | Caffeine fraction | | | Chlorogenic acid | |
|---|---|---|---|---|---|---|---|---|
| Test | Caffeine g/100 g | C* g/100 g | C % in C and caff. | Caffeine g/100 g | C g/100 g | C % in C and caff. | Caffeine g/100 g | C g/100 g |
| 1 | 1.60 | 4.50 | 73.77 | 0.41 | 0.18 | 30.51 | 0 | 0.27 |
| 2 | 1.60 | 1.60 | 50.00 | 0.31 | 0.11 | 26.19 | 0 | 0.09 |
| 3 | 1.60 | 0.53 | 24.88 | 0.24 | 0.06 | 20.0 | 0 | 0.006 |

*C = 3-chlorogenic acid

The results show that the caffeine in aqueous solution at pH 5.8 binds to itself a roughly constant chlorogenic acid quantity. In the case of a caffeine to chlorogenic acid weight ratio of 1:1 in the initial solution, the caffeine fraction contains 73.81% caffeine and 26.19% chlorogenic acid. On lowering the quantitative proportion of chlorogenic acid to less than 1:0.5 (cf. Test 3), then the total chlorogenic acid quantity was bound to caffeine (cf. FIG. 6).

EXAMPLE 9

Production of pure caffeine 420 g of the caffeine fraction contaminated with chlorogenic acids and obtained as eluate from column II according to the process of Example 2 were concentrated in a rotary evaporator to 4.9 g. A substance was obtained from the highly concentrated solution which was sucked off with a nutsch filter. The substance was washed on the filter with 2 ml of water, then again rigorously sucked off and dried for 2 hours at 110° C. in the drying oven.

0.64 g of a white substance was obtained, which was analysed with HPLC in the manner described in Example 1. The result revealed that the white substance obtained was caffeine with a purity of 99.7%.

EXAMPLE 10

Separation of caffeine from process solution

The column capacities indicated in Examples 2, 3 and 7 were increased about 100-fold, by using columns with correspondingly increased diameter. An increase of the height of the gel bed was not necessary.

Figure 7:
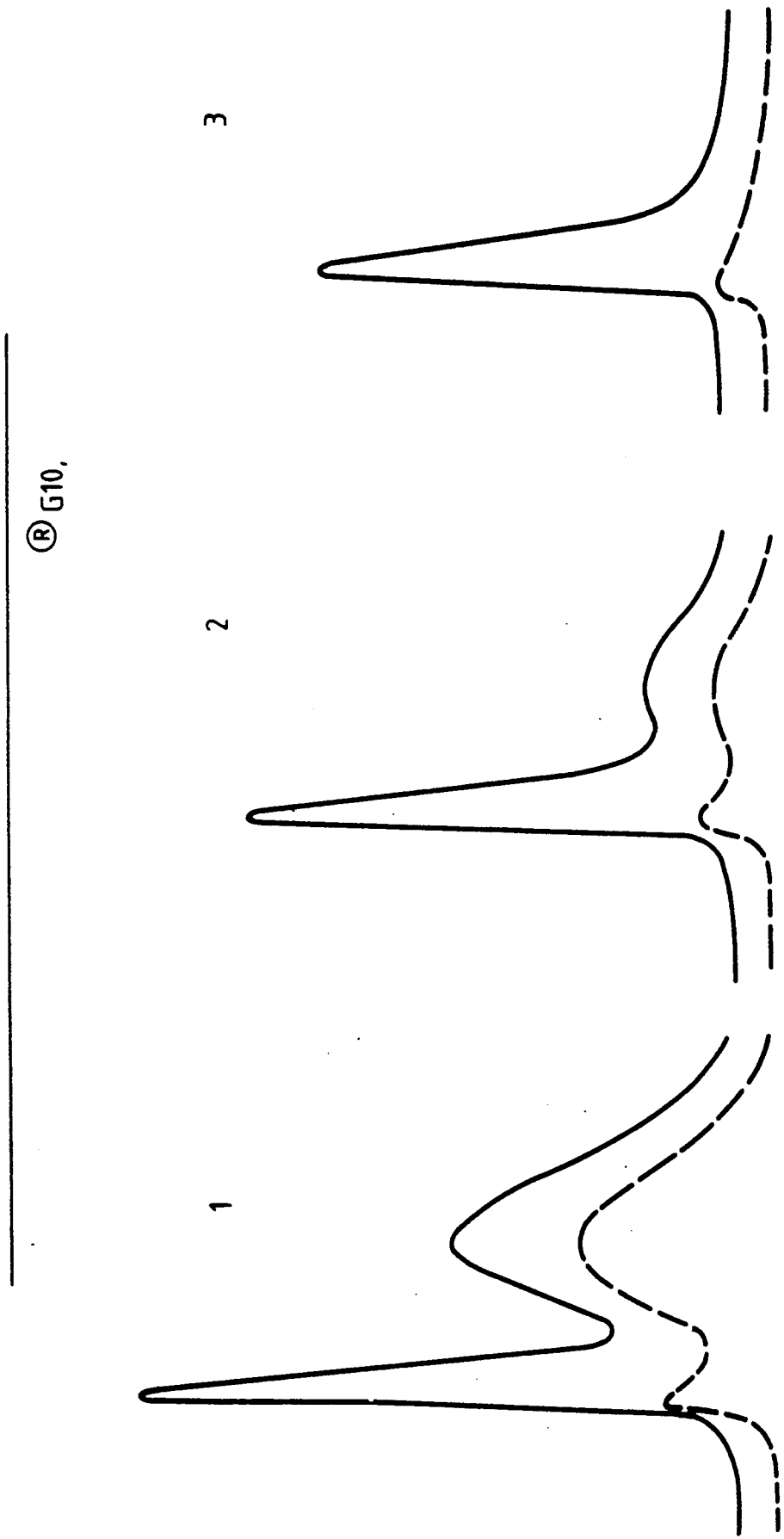
FIG. 7 is a schematic drawing of the apparatus used in the process of Example 10.

FIG. 7 shows a diagram of the separating device used in the present example. In the device column 1 had a height of 20 cm and contained 12.5 l Sephadex® G15 at 12° C. and column 2 had a height of 30 cm and contained 14.5 l Sephadex® G10 at 65° C. Differential refractometers were used as detectors and the flow rate of both columns was 30 l/hour.

The columns were separately and simultaneously eluted using two pumps with the exception of the phase where the pre-treated caffeine containing extract from column 1 was directly fed onto column 2.

The results of one separating cycle are given in Table 9.

TABLE 9

|  | Dry substance concentration (g/100 g solution) | Caffeine concentration (g/100 g solution) |
| --- | --- | --- |
| Caffeine-containing process solution | 15.96 | 0.493 |
| Process solution after removal of caffeine and concentration | 15.45 | 0.009 |

The results demonstrate that the separation patterns obtained in the large scale process are nearly identical to the patterns obtained with small columns in Examples 2, 3 and 7 and that a substantially complete separation of the caffeine was possible in only one cycle.

EXAMPLE 11

The process according to Example 10 was repeated with the exception that to increase the economical effectiveness a sequence of cycles was shifted into each other in such a manner that the fractions of each cycle would not overlap.

Figure 8:
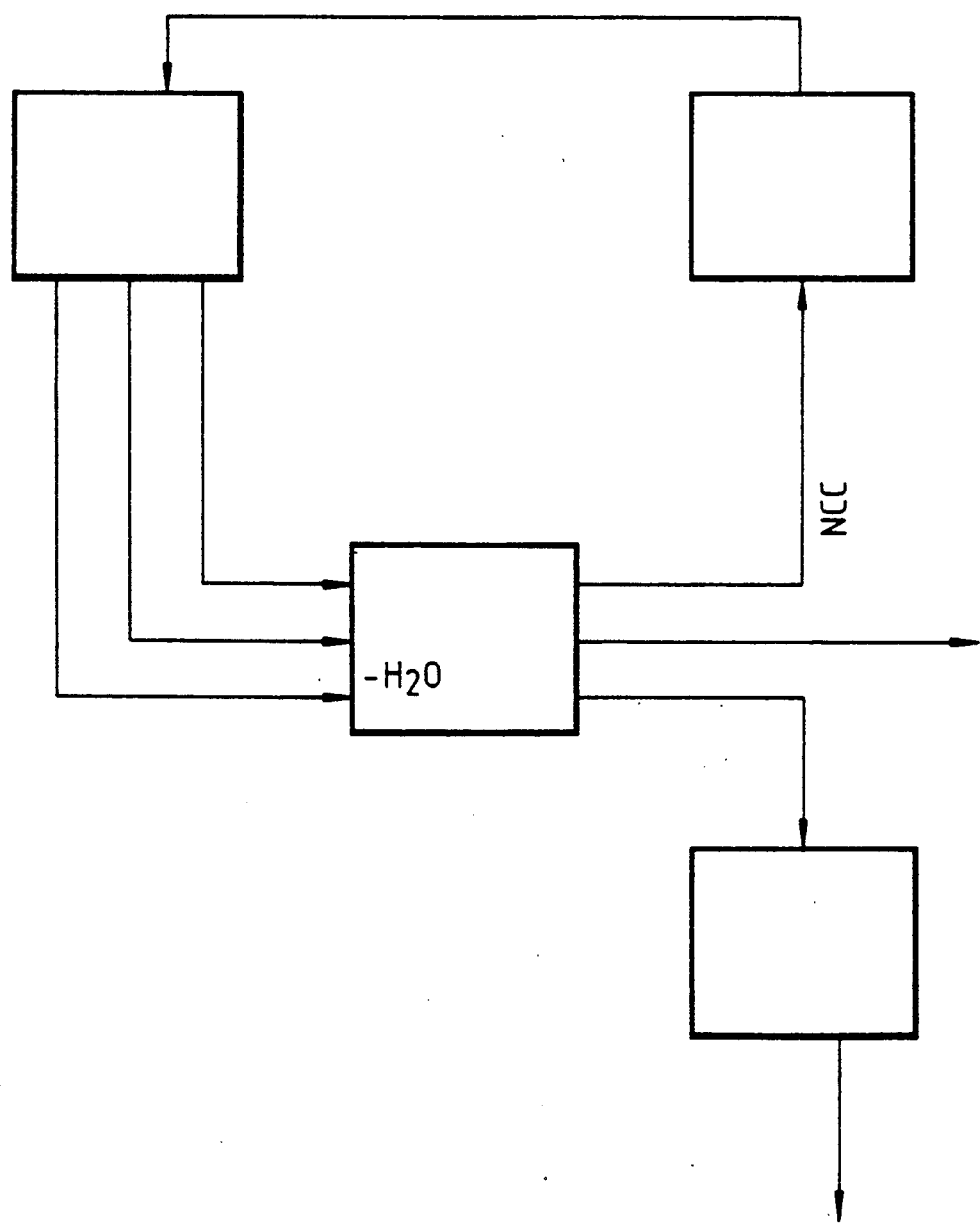
FIG. 8 shows the separation patterns according to differential refractometer measurements for the process of Example 11.

A total of 9.5 kg of caffeine-containing process solution was separated in a series of five subsequent cycles, an amount of 1.5 kg being processed in each cycle. The elution time per cycle was 45 minutes. The separation patterns of both columns during five separation cycles as recorded on a mutual recorder are shown in FIG. 8.

We claim:

1. A process for the separation of caffeine and chlorogenic acids from an aqueous raw coffee extract and from one another by means of gel permeation chromatography on a molecular sieve of crosslinked dextran with water as the eluting agent, wherein caffeine and chlorogenic acids contained in the extract are separated using at least first and second highly crosslinked dextran gels, the second or an additional gel having a higher degree of crosslinking than the first gel and having a maximum bed volume of 6 ml/g in a swollen state;
   the caffeine-containing eluate of the first gel being subsequently fed onto the second or additional gel the caffeine being obtained from the eluate of the second or additional gel at temperatures at or above room temperature.

2. A process according to claim 1, wherein the chromatography on the second gel is performed at between 40° and 80° C.

3. A process according to claim 1, wherein the chromatography on the second gel is performed at between 50° and 70° C.

4. A process according to claim 1, wherein the chromatography on the second or additional gel is performed at about 60° C.

5. A process according to claim 1, wherein the process is performed continuously and the caffeine-freed fraction of the eluate, after adjusting the same to the extract starting concentration, is used as process solution for caffeine extract production by again contacting it with raw coffee.

6. A process according to claim 2, wherein the process is performed continuously and the caffeine-freed fraction of the eluate, after adjusting the same to the extract starting concentration, is used as process solution for caffeine extract production by again contacting it with raw coffee.

7. A process according to any one of claims 5 or 6, wherein the caffeine is precipitated from the eluate in a substantially pure form by removing water.

* * * * *

UNITED STATES PATENT AND TRADEMARK OFFICE
CERTIFICATE OF CORRECTION

PATENT NO. : 5,045,334
DATED : September 3, 1991
INVENTOR(S) : KOPSCH et al.

It is certified that error appears in the above-indentified patent and that said Letters Patent is hereby corrected as shown below:

Title page, [73] Assignees: change "Kaffee-Handelsgesellschaft MBH, Federal Republic of Germany", to --Code Kaffee-Handelsgesellschaft MBH, Federal Republic of Germany--.

Signed and Sealed this

Twenty-sixth Day of April, 1994

Attest:

BRUCE LEHMAN

*Attesting Officer*  *Commissioner of Patents and Trademarks*